(12) United States Patent
Dörner et al.

(10) Patent No.: US 7,459,069 B2
(45) Date of Patent: Dec. 2, 2008

(54) ELECTROPHORESIS DEVICE AND THE USE THEREOF

(75) Inventors: Wolfgang Dörner, Mainz (DE); Renate Konrad, deceased, late of Bad Soden (DE); by Raimund Konrad, legal representative, Bad Soden (DE)

(73) Assignee: Institut fur Mikrotechnik Mainz GmbH (DE)

(*) Notice: Subject to any disclaimer, the term of this patent is extended or adjusted under 35 U.S.C. 154(b) by 859 days.

(21) Appl. No.: 10/471,984

(22) PCT Filed: Mar. 18, 2002

(86) PCT No.: PCT/DE02/00974

§ 371 (c)(1),
(2), (4) Date: Mar. 8, 2004

(87) PCT Pub. No.: WO02/075298

PCT Pub. Date: Sep. 26, 2002

(65) Prior Publication Data

US 2004/0144647 A1      Jul. 29, 2004

(30) Foreign Application Priority Data

Mar. 19, 2001   (DE) ................................ 101 13 257

(51) Int. Cl.
*G01N 27/447*   (2006.01)
*G01N 27/453*   (2006.01)

(52) U.S. Cl. ........................ 204/451; 204/455; 204/459; 204/601; 204/605; 204/610

(58) Field of Classification Search ................. 204/451, 204/455, 459, 600, 601, 605, 610
See application file for complete search history.

(56) References Cited

U.S. PATENT DOCUMENTS 4,101,401 A    7/1978   Hoefer (Continued)

FOREIGN PATENT DOCUMENTS

| DE | 198 26 020 | 12/1999 |
|----|------------|---------|
| EP | 0 544 969  | 6/1993  |
| EP | 0 977 030  | 2/2000  |

OTHER PUBLICATIONS

H. Becker et al., Planar quartz chips with submicron channels for two-dimensional capillary electrophoresis applications, Journal of Micromech. & Microeng., New York, NY, vol. 8, No. 1, Mar. 1, 1998, pp. 24-28, XP-002088541.
A. Gorg et al, The current state of two-dimensional electrophoresis with immobilized pH gradients, Electrophoresis 2000, Weinheim, Germany, vol. 21, No. 6, Apr. 2000, pp. 1037-1053, XP-001015374.
"High Resolution Two-Dimensional Electrophoresis of Proteins", Patrick H. O'Farrell, The Journal of Biological Chemistry, vol. 250, No. 10, Issue of May 25, pp. 4007-4021, 1975.

(Continued)

*Primary Examiner*—Kaj K Olsen
(74) *Attorney, Agent, or Firm*—Hudak, Shunk & Farine Co. LPA

(57) ABSTRACT

The invention relates to a device for electrophoretically separating molecules. The inventive device comprises: at least one plate having a top side and an underside; a first separating channel provided for receiving at least one first separating medium; at least one second channel, which is orthogonal to said first separating channel and which is provided for receiving a second separating medium; optionally comprises implements provided for filling the device with reagents, solvents, buffers, separating media and/or for loading the device with a sample to be separated, and; terminals for applying electric separating voltage to the separating channels. In the device, the first separating channel is located on the plate top side and comprises at least one first opening that leads to the plate underside, whereby the second separating channel is located on the plate underside and comprises at least one second opening. The first opening of the first channel and the second opening of the second channel are connected to one another.

20 Claims, 3 Drawing Sheets

U.S. PATENT DOCUMENTS

| | | | |
|---|---|---|---|
| 4,385,974 A | | 5/1983 | Shevitz |
| 5,599,432 A | | 2/1997 | Manz et al. |
| 6,013,165 A | * | 1/2000 | Wiktorowicz et al. ....... 204/456 |
| 6,284,113 B1 | * | 9/2001 | Bjornson et al. ............ 204/453 |
| 6,607,644 B1 | * | 8/2003 | Apffel, Jr. ................... 204/451 |

OTHER PUBLICATIONS

"Adaptation of Capillary Isoelectric Focusing to Microchannels on a Glass Chip", Oliver Hofmann, Diping Che, Kenneth A. Cruickshank, And Uwe R. Müller, Anal. Chem. 1999, 71, 678-686.

"Room-Temperature Imprinting Method for Plastic Microchannel Fabrication", Jingdong Xu, Laurie Locascio, Michael Gaitan, and Cheng S. Lee, Anal. Chem. 2000, 72, 1930-1933.

"SDS Capillary Gel Electrophoresis of Proteins in Microfabricated Channels", Shao Yao, Deon S. Anex, W. Brett Caldwell, Don W. Arnold, Katherine B. Smith, and Peter G. Schultz, Proc. Natl. Acad. Sci. USA, vol. 96, pp. 5372-5377, May 1999 Chemistry.

* cited by examiner

ELECTROPHORESIS DEVICE AND THE USE THEREOF

CROSS REFERENCE

This application is a 35 U.S.C. § 371 application of PCT DE02/00974 filed on Mar. 18, 2002, which in turn claims priority to German Application No. 101 13 257.3, filed on Mar. 19, 2001.

FIELD OF THE INVENTION

The present invention relates to an electrophoresis device. The invention further relates to the use of this device for a two-dimensional electrophoretic separation of macromolecules.

BACKGROUND OF THE INVENTION

Two-dimensional gel electrophoresis (2D gel electrophoresis) is a conventional method for separating, e.g., complex protein mixtures. This method typically consists of two electrophoresis steps that are carried out separately and successively, namely isoelectric focusing (IEF) (1st dimension) and denaturing SDS polyacrylamide gel electrophoresis (SDS-PAGE) (2nd dimension). IEF, as a rule, is performed in polyacrylamide gel strips or gel rods with immobilized pH gradients. Immobilized pH gradients are distinguished in that the buffer substances are covalently bound in the polymer; they no longer have to be applied together with the sample. The gradient is thus fixed within the gel. As an alternative thereto, normal polyacrylamide gel may be used if ampholytes are applied together with the sample. The fixed pH gradient is obtained by dipping the corresponding ends of the gel into an acid buffer (anolyte) and an alkaline buffer (catholyte). In a subsequently applied electric field, the ampholytes migrate into their specific isoelectric region and thereby establish and stabilize the pH gradient. The molecules to be analyzed migrate in the electric field to the position where the gradient has a pH value corresponding to the isoelectric point of the molecule. Thus the proteins are separated in this first direction irrespective of their size or mobility and exclusively based on their isoelectric properties. After completion of IEF and optional treatment in separate vessels with different mobilization and washing powders, the gel strips or gel rods are placed onto a typically vertical SDS-PAGE gel that is placed into an electrophoresis apparatus. When a voltage is applied, the proteins are transported out of the gel strip/gel rod of the 1st dimension and into the SDS-PAGE gel, where they are separated in a 2nd direction according to their molecular mass.

Both of these methods may in principle also be implemented in a capillary electrophoretic technique and are then referred to as CIEF and CGE, respectively.

After the first publication of a 2D electrophoresis method (P. H. O'Farrel 1975 *J. Biol Chem.* 250, 4007-4021), methods and devices were developed to allow the two methods to be carried out in a single apparatus or a single gel (J. Shevitz 1983: *Electrophoretic system and method for multidimensional analysis*; U.S. Pat. No. 4,385,974 and S. A. Hoefer 1978: *Fluid isolation electrophoresis apparatus and method*; U.S. Pat. No. 4,101,401). These documents already describe approaches for the parallel processing of a plurality of samples. With commercially available systems (Dalt system, Hoefer Scientific Instruments, San Francisco, Calif., USA) it is possible, for example, to subject up to 12 samples simultaneously to IEF and to run up to 10 SDS PAGE gels in a single operation. A clear miniaturization of these electrophoresis methods has thus far been achieved by making the gels smaller and by introducing a partially automated electrophoresis system.

During the last few years, the capillary electrophoretic methods have also been further developed using microsystem technology. The trend is to produce chips on which the electrophoresis elements are mounted in miniaturized form. Known in the art are the use of suitable chips for CIEF of proteins (O. Hofman, D. Che, K. A. Cruickshank & U. Müller 1999: *Adaptation of capillary isoelectric focusing to microchannels on a glass chip*. Anal. Chem. 71, 678-686 and J. Xu, L. Locascio, M. Gaitan & C. S. Lee 2000: *Room temperature imprinting method for plastic microchannel fabrication*. Anal. Chem. 72, 1930-1933) as well as the SDS gel based separation of proteins (S. Yao, D. S. Anex, W. B. Caldwell, D. W. Arnold, K. B. Smith & P. G. Schultz 1999: *SDS capillary gel electrophoresis of proteins in microfabricated channels*. Proc. Natl. Acad. Sci. USA 96, 5372-5377). Solutions are known, for example, which generally propose to combine two electrophoresis techniques that are orthogonal to one another, as described, for example, in U.S. Pat. No. 5,599,432.

It is generally known that conventional 2D gel electrophoresis is very time-consuming. The analysis of a sample can take up to approximately 2 days. Because of the many complex work steps involved, the method can be carried out only by specially trained technical personnel.

It has been found that automation is possible only to a limited extent. Partially automated commercially available systems (e.g. the Phast system) still require many manual work steps. The dimensions of the gel apparatuses that have been used until now permit parallel analyses only to a limited extent (approximately 10 samples) but no high throughput analyses.

U.S. Pat. No. 4,385,974 describes a two-dimensional separation method and an apparatus for carrying out successively both IEF and, perpendicularly thereto, SDS-PAGE without any gels or gel pieces having to be moved. An electrically non-conductive fluid barrier, preferably glycerin, is arranged between the IEF gel and the SDS-PA gel. After completion of the first IEF separation step, this fluid barrier is aspirated using a tip and is replaced with an equilibration buffer. This method, however, still requires many additional manual steps: casting and polymerizing the SDS-PA gel, covering with a layer of glycerin, casting and polymerizing the IEF gel, installing the gel cassette in the device, filling the reservoir, etc. As a result, this complex method precludes full automation.

The use of a single plate gel for both work steps as described in U.S. Pat. No. 4,101,401 leads to insufficient resolution of the protein bands because of the very different requirements to be met by the composition of the two separation matrices. Attempts have also been made to carry out multi-dimensional electrophoresis on a microscale basis. U.S. Pat. No. 6,013,165, for example, describes two devices. The first is suitable for the conventional combination of IEF and SDS-PAGE and is provided with a cavity, whereas the second contains a field traversed by a plurality of parallel microchannels and can be used for carrying out alternative 2D-methods. This document does not describe any approaches to automating the conventional method, which requires rebuffering or protein mobilization steps, among others.

SUMMARY OF THE INVENTION

One object of the present invention is to provide electrophoresis systems which can be completely automated and in which the number of manual steps required can be reduced or even eliminated. A further object of the invention is to miniaturize the execution of electrophoresis systems to the point where several or many chromatographic or gel separations can be performed in parallel and the separation or analysis is accelerated.

These objects were attained with the inventive device in accordance with the features set forth in claim 1. The dependent claims define preferred embodiments.

The device according to the invention in its simplest embodiment consists of a plate with a topside and an underside. On one side, e.g. on the topside, this plate has a first separation channel and on the underside at least one second separation channel that extends orthogonally to the first separation channel. In a simple embodiment, the first separation channel is configured as a recess or groove formed in the topside of the plate and has at least one opening to the underside of the plate, which is referred to as the first opening or the first passage opening. The second separation channel, in a simple embodiment according to the invention, is likewise configured as an oblong recess extending along the surface of the underside of the plate. This second separation channel advantageously extends up to the first opening of the first channel on the underside or extends beyond this opening. At the point where the second separation channel meets the first dower) opening of the first channel, i.e., at the point where the two channels meet or intersect, an opening is created in the floor of the second separation channel which is directed toward the interior of the plate and which is referred to as the second opening of the second channel. Via these openings the two separation channels are connected with one another. This arrangement of the separation channels or electrophoresis channels according to the invention in which the separation paths or tracks of the first and the second dimension lie in different non-intersecting planes makes it possible to design an electrophoresis device as a disposable unit that is easy to manufacture. In a preferred embodiment, the device according to the invention is configured as a miniaturized ready-made chip.

In a particularly preferred embodiment, the first separation channel and the second separation channel are interconnected or separated by a gap. The gap is arranged between the first opening of the first separation channel and the second opening of the second separation channel. At its upper end, this gap terminates at the first opening of the first separation channel and at its lower end at the second opening of the second separation channel.

In principle, it is possible to use the device, which can be adapted to and inserted into an automated analyzer, without any further covers, i.e. with the upper sides of the channels open. This is true, in particular, if it is configured as a chip for analyzers, particularly devices that work automatically. It has been found to be advantageous, however, to seal the device according to the invention along its topside and underside with an additional plate or foil. If the device is sealed by additional plates, it is of course possible to arrange individual elements of the device in the sealing or cover plates. For example, the second separation channel, or preferably a plurality of second separation channels, can be arranged in the topside of a lower cover plate. It is also possible to arrange or emboss elements in these cover plates or sealing plates to fill the device with reagents, solvents, buffers, separation media for introducing or connecting electrodes and/or for charging a sample to be separated, which would otherwise be arranged on the plate with the first channel or, in the case of a one-piece configuration, on the one single plate.

The cover plates and the main plate can be interconnected with conventional bonding or gluing methods, e.g. solvent bonding.

The plates themselves may be produced by simple methods familiar to the person skilled in the art, e.g. injection molding or hot embossing. The plates are preferably made of materials suitable for conventional embossing, extrusion or injection molding techniques. To be mentioned as examples of a suitable polymer material are PMMA, polycarbonate, polyethylene terephthalate, polystyrene or PDMS. Elastomer plastics are preferred. In many cases it may be preferred to make the plates of a transparent plastic so that they are suitable for known absorption analysis methods. This makes it possible to use analysis methods familiar to the person skilled in the art for locating and determining the concentration of certain proteins.

In a further embodiment according to the invention, the rear side of the device is provided with a reflective material. This enables, for example, incident light of a specific wavelength to penetrate, e.g., the second separation channels from the top, such that the substance to be analyzed absorbs a portion of the light at characteristic wavelengths. After reflection on the underside, the light penetrates the sample to be analyzed a second time, so that further absorption occurs. This makes it possible to refine the analysis and to make it more sensitive.

The first channel is usually but not necessarily formed as a channel open to the topside of the plate. It has typically a round, curved, but preferably rectangular or possibly triangular cross section. A square cross section is preferred to the rectangular cross sections. In another particularly preferred embodiment, the cross section of the first channel tapers in the direction of the plate's underside. The first separation channel also has a first opening in the direction of the plate's underside. In other words, it is open to the underside of the plate. Analyte molecules separated in the first dimension can be guided through this opening to the second separation channels for further separation in the second dimension. In a preferred embodiment, the first separation channel is open to the bottom over its entire length.

In a likewise particularly preferred embodiment, a partition plate, particularly a porous or permeable partition plate that bounds the first separation channel at the bottom, is disposed at this first opening to the plate's underside. This partition plate is permeable, however, for analyte molecules or sample molecules as well as for electrolytes and preferably solvents. Such plates can be made of any material that is inert to or compatible with the samples and the reagents or electrolyte buffer solutions used, e.g. agarose, porous plastics and/or solid gels. In principle, it is also possible to use non-porous impermeable plate materials if they can be removed or made porous by suitable solvents or reagents without damaging the analysis system and the analytes.

The first channel is advantageously 1 to 20 cm long, preferably 1.5 to 5 cm. It is preferably 20 µm deep or wide, advantageously at least 50 µm. Preferred maximum depths or widths are 2000 µm, preferably 1500 µm and particularly preferably 1000 µm.

The second separation channel typically has a round, square or even a triangular cross section and is preferably open to the plate's underside over its entire length. It is advantageously formed as a capillary. In a particularly preferred embodiment, the device has a plurality of such second channels, advantageously, however, at least 100, preferably at least 200, particularly preferably at least 250. The length of the second channels is usually 1 to 20 cm, preferably 1.5 to 15 cm, with 2 to 12 or 5 to 10 cm being particularly preferred. The preferred width is 5 to 200 µm, with 10 to 150 and 20 to 100 cm being particularly preferred. The usual depths again correspond to the width and preferably are 5 to 200, particularly preferably 20 to 100 µm.

A particularly preferred embodiment according to the invention has a gap between the first separation channel and the second separation channel. This gap is advantageously also formed as a channel and preferably extends elongated underneath the first separation channel. In a particularly preferred embodiment it has a cross section tapering in the direction toward the second channel. The cross section of the gap is especially triangular or funnel-shaped and preferably ends in a small collecting channel, which opens out laterally or from above into the second opening of the second separation channel(s). The gap, which preferably serves as a collection chamber or a concentration chamber, has a cross-sectional diameter in its upper part of preferably at least 20 µm, particularly at least 50 µm and preferably at most 2000 µm, particularly at most 1500 µm and in its lower part preferably at least 5 µm, particularly at least 10 µm and advantageously at least 20 µm and preferably at most 400 µm, particularly at most 200 µm.

The device according to the invention further comprises facilities for receiving electrodes, buffer electrolyte solutions, etc. and connections for loading and/or removing buffer solutions, electrolyte solutions, or reagents, which are in fluidic communication with the first and second separation channels or with the gap. Because the amounts of separating agents, electrolyte-ampholyte reagents or buffer solutions are small they can be arranged in reservoirs directly on the plate, e.g. in the form of recesses or cutouts.

The electrodes are preferably metallic conductors arranged directly in the device. It is also possible, however, to form the electrodes as electrolytes or electrolyte solutions, which then connect the separation channels with an external electrical conductor.

Suitable separating agents for the device according to the invention are all the known agents used, for example, for isoelectric focusing. For the second channels, typically all the gels that are suitable for capillary gel electrophoresis and, in particular, PAGE electrophoresis can normally be used. For example dextrans, agaroses, celluloses, polyvinylpyrrolidone, polyvinyl alcohol and derivates of these compounds as well as other natural or synthetic polymers and mixtures thereof may be used. According to the invention it is also possible, however, to load the second separation channel with conventional separation media used for chromatographic separation methods, i.e. those used, for example, in high-pressure chromatography (HPLC) or in conventional column chromatography, e.g. silica gels or sepharose.

The invention further relates to the use of the inventive device for analyzing samples, for isolation, preparative cleaning and recovery of substances, e.g. proteins and/or charged particles. The inventive device has proven suitable especially for analyzing proteomes and genomes.

In the use according to the invention the procedure is typically that the device, which is preferably configured as a chip, particularly a miniaturized chip. It is loaded by filling a gel matrix into the first separation channel or, optionally, via reservoirs with electrolyte and/or buffer solutions, optionally via reservoirs. Thereafter, a solution with the sample to be analyzed, particularly containing macromolecules, is applied to the separation or gel matrix. When a voltage is applied to the electrodes, which are immersed, for instance, in the electrolyte or buffer reservoirs at the two ends of the first separation channel, the analyte molecules to be analyzed are electrophoretically separated. A preferred electrophoresis method for the first separation channel is isoelectric focusing. When isoelectric focusing is completed, the electrolyte solutions are removed or replaced and, optionally, replaced with mobilization buffers.

In a particularly preferred embodiment, the gap, which has previously been filled with air or an electrically non-conductive medium, is filled with a stacking gel. This filling process and the removal of electrolytes and buffers in the other channels can be done, for example, by aspiration via a reservoir or by means of the devices provided for filling and removal. If a partition plate is arranged between the gap—preferably disposed underneath the separation channel as an intermediate channel—and the first separation channel, it may be preferred to use agents in the stacking gel solution of the gap or the buffer introduced thereby which dissolve the partition plate or make it at least porous or permeable.

In principle, it is also possible to introduce reactive substances into the gap. Such substances can be, for example, marker substances, immunoreagents or substances for enzyme reactions, so that the analyte molecules react therewith as they pass through or reside in the gap. It is furthermore possible, for instance, to derivatize the analyte molecules in the gap by acetylation or glycosylation. This derivatization may make the marking of the analyte molecules possible in the first place.

The separated analyte molecules that are present at various locations in the first separation channel are then transported by means of a uniform high voltage—generated by an electrode and applied between the first separation channel and the second separation channel—from the first separation channel to the stacking gel, where they are concentrated. This concentration is further enhanced by the preferred downwardly tapering cross-sectional shape of the gap. From the gap, the analyte molecules, due to the applied voltage, are then transported through the second opening of the second separation channels into the second separation channels where they are further separated by means of the same electrodes or, optionally, by additional electrodes disposed at opposite ends of the second separation channels.

The analyte molecules thus separated are detected using conventional methods familiar to one skilled in the art, e.g. by detecting radioactive radiation, by dyeing techniques and/or by absorption and/or emission of light, particularly UV and UV/VIS light. The device according to the invention is preferably used in automated analyzers adapted therefor. It is particularly suitable for separating, cleaning and isolating as well as for preparative recovery of RNA, DNA and proteins from genomes and proteomes.

BRIEF DESCRIPTION OF THE DRAWINGS

The invention will now be described with reference to the figures in which.

DETAILED DESCRIPTION OF THE INVENTION

Figure 1:
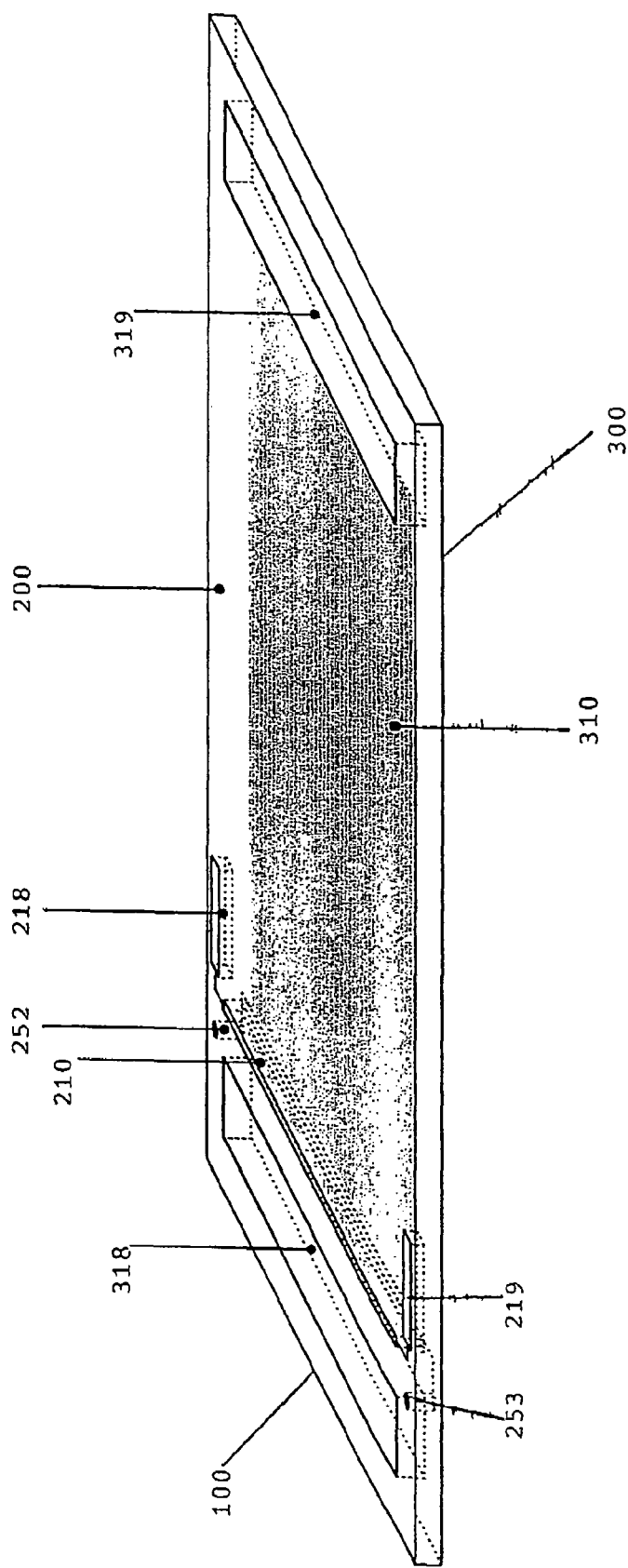
FIG. 1 depicts a one-piece embodiment with only a single plate.

All the separation and junction paths required to carry out electrophoresis systems and the structural elements for sample application and concentration as well as the devices for feeding separation media, buffer solutions and reagents are preferably accommodated on a single plate as shown in FIG. 1. In principle, however, it is also possible to arrange individual elements on separate plates that are then used, for example, as cover plates. This is shown by way of example in FIG. 2 where the device 100 according to the invention, for the sake of clarity, is depicted in an arrangement of two micro-structured plates 100, 360.

The device, can be configured, for example, as a miniaturized chip and can have the size of a credit card.

The plate 100 has reservoirs 218, 219, 318, 319 for buffer and/or electrolyte solutions and a first separation channel 210 as well as a buffer inlet 252 communicating with a gap 250 and a buffer discharge 253.

Figure 2:
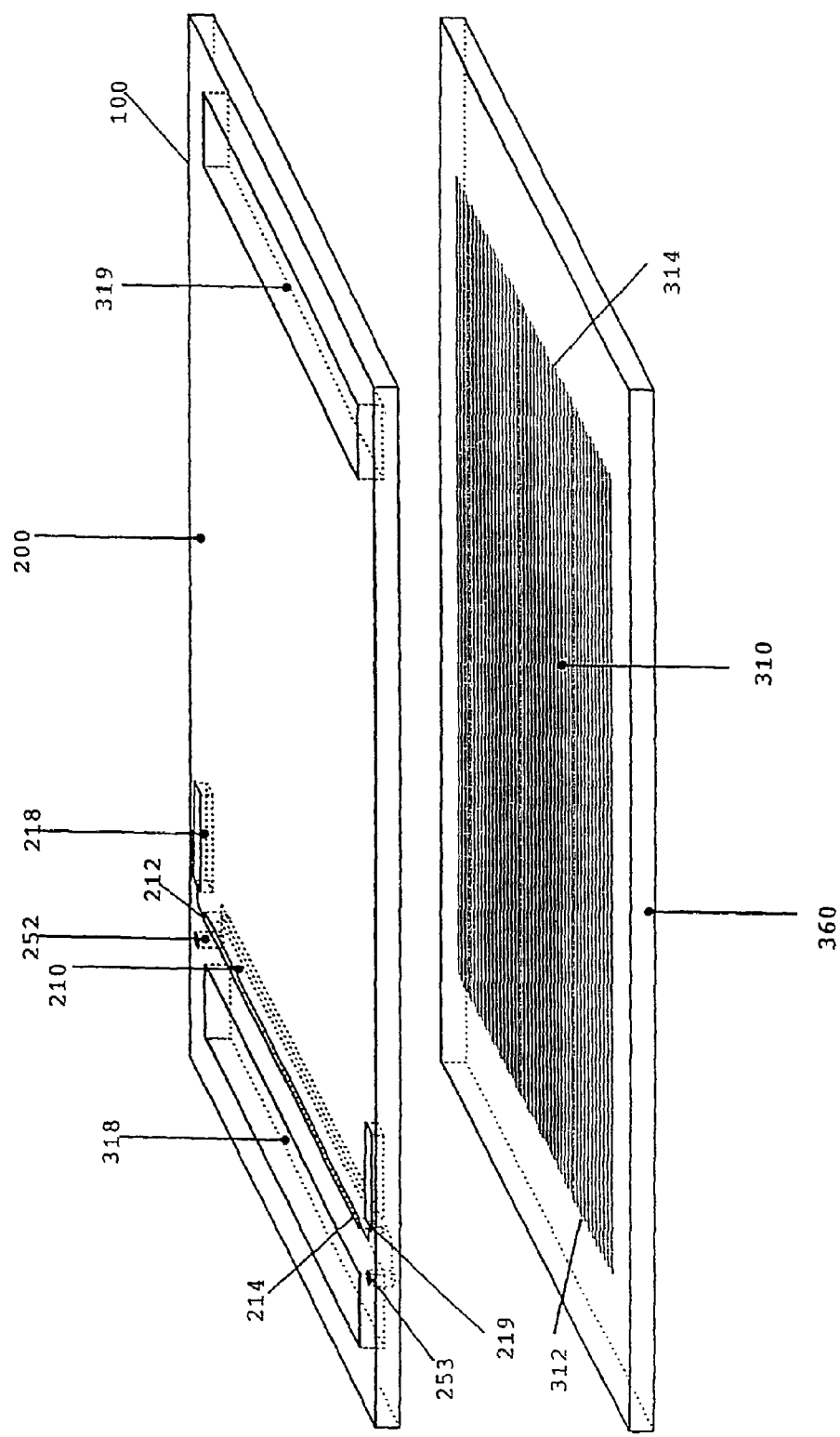
FIG. 2 is a schematic representation of a two-piece embodiment of the device according to the invention.

The plate's underside 300 of FIG. 1 or the bottom plate 360 of FIG. 2 has a plurality of second separation channels 310 formed therein.

The first separation channel 210 normally has a rectangular cross section. In one embodiment of the present invention, the first separation channel 210 is wide in its upper part and narrow in its lower part. The diameter in the upper part of the first separation channel 210 can range, for example, from 500 to 1000 μm, while the diameter in the lower part of the first separation channel 210 ranges from 20 to 200 μm.

Figure 3:
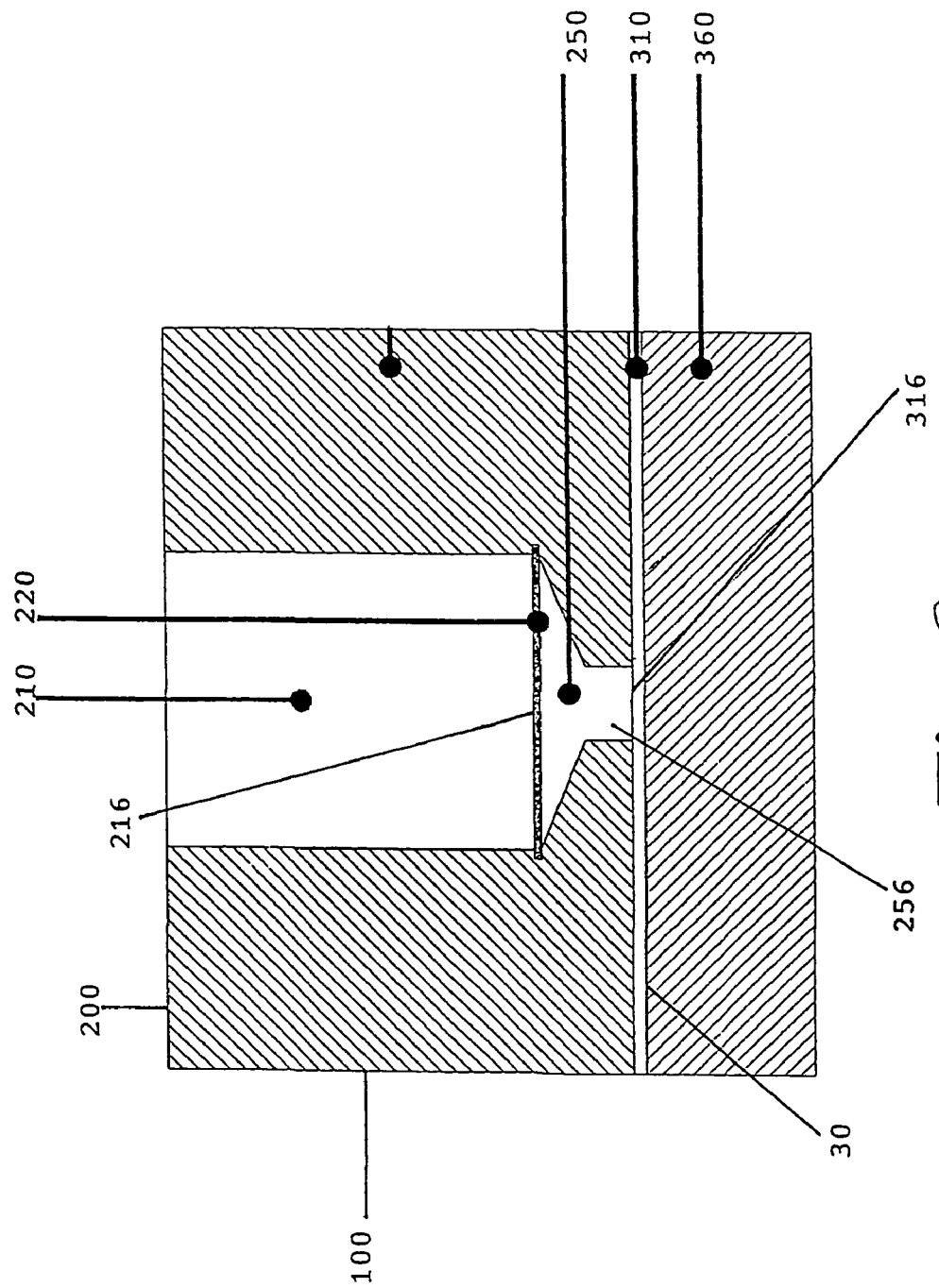
FIG. 3 is a schematic cross-sectional view of the assembled device depicted in FIG. 2, where a section was made through the first separation channel.

In a further embodiment depicted in FIG. 3, the first separation channel 210 has a partition wall or a partition plate 220 which is porous or permeable or which can be transformed into a porous permeable state, or can even be dissolved entirely, after completion of the first electrophoresis (IEF). This partition wall 220 separates the first separation channel 210 from the gap 250. As may be seen in FIG. 3, the gap 250 tapers in a funnel shape in downward direction and opens out into a small collection or transfer passage 256, which terminates at the second opening 316 of the second channel 310.

The plate underside 300 normally has a plurality, preferably several hundred parallel second separation channels 310. The plate 100 is preferably made of a plastic material.

The separation channels 310 of the second dimension can be filled, for example, as follows. The openings of the reservoirs 218, 219, the buffer inlet 252 and the buffer discharge 253 and those of the first separation channel 210 are sealed with adhesive tape, a piece of foil or a plate (not depicted).

The reservoir 319 is filled with a monomer or polymer solution. Suitable monomers are, for example, any of the gel-forming monomers typically used for such techniques. By applying a slight negative pressure to reservoir 318, the solution is transported into the separation channels 310 until these channels are completely filled. If a monomer solution is used, polymerization can be effected in a manner known per se by means of catalysts already contained in the solution and/or by exposure to light.

The separation path, the length of which corresponds to approximately the length of the first separation channel 210 in the plate 100 and which is assigned to the first dimension, can be filled as follows. The separation path of the first dimension, i.e. the first separation channel 210, can be filled by introducing a buffer, monomer or polymer solution into the reservoir 218, 219, possibly by applying a positive or negative pressure.

Finally, the separation path, i.e. the first separation channel 210 of the first dimension can be connected with the separation channels 310 of the second dimension as follows. By introducing a buffer, monomer, or polymer solution into the buffer inlets 252, the gap 250 is filled and a connection is thereby established between the first and the second dimension. Because the gap 250 thus filled with a gel can also be used for separation or even for carrying out reactions, it is possible to use up to three different separating or reaction matrices in a system.

As mentioned above, the analysis device configured as a chip according to the invention is excellently suited for a two-dimensional electrophoresis. In the first separation channel 210, which corresponds to the first dimension, isoelectric focusing is carried out. In the second separation channels 310 on the plate underside 300, which correspond to the second dimension, SDS polyacrylamide gel electrophoresis is then carried out using the analytes from the isoelectric focusing.

In one embodiment of the use according to the invention, a two-dimensional gel electrophoresis is carried out as follows. The isoelectric focusing takes place in the first separation channel 210. For this purpose, a gel matrix is filled into the first separation channel 210, while electrolyte solutions are put into the buffer reservoirs 218, 219. As may be seen also in FIG. 3, for example, the first separation channel 218 for the isoelectric electrophoresis is separated from the separation channels 310 filled, for example, with polyacrylamide by a partition wall 220 and a gap initially filled with air or a non-conductive solvent.

After introducing the IEF separation medium (e.g. an ampholyte solution in agarose or polyacrylamide) into the upper part of the first separation channel 210 and acid and lye as electrolyte solutions into the reservoirs 218, 219 provided therefor as well as the protein sample, an electric voltage is applied in accordance with a defined protocol. After completion of the isoelectric focusing, the IEF electrolyte solutions are discharged and an additional electrophoresis buffer is introduced into the buffer reservoirs 218, 219.

The old electrolyte solution is optionally replaced with a mobilization solution. After an incubation phase, this solution is then replaced with an electrode buffer.

The gap 250 underneath the first separation channel 210 is then filled with stacking gel solution through the inlet 252. By applying a high voltage to electrodes in the reservoirs. 318, 319 and the first separation channel 210 (218, 219), analyte molecules are transported from the upper part of the first separation channel 210 through the partition wall 220 into the funnel-shaped part of the gap 250. Here, the analyte molecules are concentrated. By applying a further voltage, the concentrated analyte molecules are dosed into the second separation channels 310 where they are separated according to their molecular mass and can be subsequently optically detected in the chip through the plate topside 200 or the underside 300 or by other means through additional integrated structures.

In a preferred embodiment, the stacking solution contains a substance for making the partition wall 220 in the first separation channel 210 permeable.

With the two-dimensional gel electrophoretic method according to the invention, all mixtures of macromolecules can be effectively separated. To be cited here as examples are protein mixtures or nuclein mixtures.

A particular advantage of the chip according to the invention is that the entire microfluidic separation system is divided into two or three 3-dimensionally arranged compartments that can be filled independently from one another. All of these compartments are integrated into the chip. This division makes it possible to carry out, for example, the conventional two-dimensional gel electrophoresis on a miniaturized scale on a chip, which can be operated fully automatically by means of a suitable operator device. Particularly advantageous is the use of the funnel shaped gap 250 for sample concentration. If there is an electric potential gradient across this structure, the special geometry attributable to the taper of the funnel and thus the increasing density of the electric field lines cause the charged analyte molecules to be concentrated spatially and over time. The chip according to the invention makes it possible to combine the efficiency of the conventional two-dimensional gel electrophoresis with the high resolution of capillary electrophoresis and to shorten the analysis times by using microstructures. The arrangement of inlets and reservoirs on the device as well as the configuration of miniaturized chips, particularly ready-made chips, makes it possible to automate the entire analysis.

LIST OF REFERENCE NUMERALS 100 main plate
200 plate topside
300 plate underside
210 first channel
212, 214 opposite ends of the first channel first opening
216 first opening
218 reservoir of the first channel communicating with the end 212
219 reservoir of the first channel communicating with the end 214
220 partition wall
250 gap
252 buffer inlet
253 buffer discharge
256 gap passage
310 second channel
312, 314 opposite ends of the second channel
316 second opening
318 reservoir communicating with the end 312 of the second channel
319 reservoir communicating with the end 314
316 bottom plate

The invention claimed is:

1. A device for electrophoretically separating molecules, comprising: at least one plate having a topside and an underside, a first separation channel configured to receive at least one first separation medium, at least one second separation channel that is orthogonal to the first separation channel and is configured to receive a second separation medium and, optionally, facilities for filling the device with reagents, solvents, buffers, separation media or for loading it with a sample to be separated, or a combination thereof; optionally, terminals for applying an electric separation voltage to the first and second separation channels; wherein the first separation channel is disposed on the plate's topside and has at least one first opening to the plate's underside, and the second separation channel is disposed on the plate's underside and has at least one second opening, such that the first opening of the first separation channel and the second opening of the second separation channel are interconnected, and wherein the first opening of the first separation channel is sealed by a permeable partition wall.

2. The device as claimed in claim 1, wherein a gap is arranged between the first separation channel and the second separation channel through which the first opening and the second opening are interconnected.

3. The device as claimed in claim 2, wherein the gap is configured as an intermediate channel extending underneath the first separation channel.

4. The device as claimed in claim 2, wherein the gap has a funnel-shaped cross section.

5. The device as claimed in claim 2, wherein the first and the second separation channels as well as the gap can be filled separately from one another.

6. The device as claimed in claim 2, wherein the first separation channel has a rectangular or a funnel-shaped cross section, or a combination thereof.

7. The device as claimed in claim 6, wherein the gap is configured as an intermediate channel extending underneath the first separation channel.

8. The device as claimed in claim 7, wherein the gap has a funnel-shaped cross section.

9. The device as claimed in claim 1, wherein the first separation channel has a rectangular or a funnel-shaped cross section, or a combination thereof.

10. The device as claimed in claim 1, wherein the device has a cover that at least partially seals the topside or the underside, or a combination thereof.

11. The device as claimed in claim 10, wherein the cover is a further plate or a foil, or a combination thereof.

12. The device as claimed in claim 11, wherein the cover at least partially seals the underside and is a further plate, which comprises a surface facing the plate on which the second separation channel is arranged.

13. The device as claimed in claim 12, wherein a plurality of second separation channels are present, and wherein the second separation channels are capillary separation channels that extend in parallel.

14. The device as claimed in claim 13, wherein a gap is arranged between the first separation channel and the second separation channel through which the first opening and the second opening are interconnected, and wherein the first and the second separation channels as well as the gap can be filled separately from one another.

15. The device as claimed in claim 10, wherein the cover at least partially seals the underside and is a further plate, which comprises a surface facing the plate on which the second separation channel is arranged.

16. A device as claimed in claim 1, wherein a plurality of second separation channels are present, and wherein the second separation channels are capillary separation channels that extend in parallel.

17. A method for electrophoretically separating molecules, comprising the steps of:
providing a device comprising at least one plate having a topside and an underside, a first separation channel configured to receive at least one first separation medium, at least one second separation channel that is orthogonal to the first separation channel and is configured to receive a second separation medium and, optionally, facilities for filling the device with reagents, solvents, buffers, separation media or for loading it with a sample to be separated, or a combination thereof, as well as terminals for applying an electric separation voltage to the first and second separation channels, wherein the first separation channel is disposed on the plate's topside and has at least one first opening to the plate's underside, and the second separation channel is disposed on the plate's underside and has at least one second opening, such that the first opening of the first separation channel and the second opening of the second separation channel are interconnected, and wherein the first opening of the first separation channel is sealed by a permeable partition wall; and
using the device for analyzing samples, or isolating, cleaning and recovering chemical substances utilizing the device.

18. The method as claimed in claim 17, wherein the chemical substances are RNA, DNA or a protein or a combination thereof.

19. A method for electrophoretically separating molecules, comprising the steps of:

providing a device comprising at least one plate having a topside and an underside, a first separation channel configured to receive at least one first separation medium, at least one second separation channel that is orthogonal to the first separation channel and is configured to receive a second separation medium and, optionally, facilities for filling the device with reagents, solvents, buffers, separation media or for loading it with a sample to be separated, or a combination thereof, as well as terminals for applying an electric separation voltage to the first and second separation channels, wherein the first separation channel is disposed on the plate's topside and has at least one first opening to the plate's underside, and the second separation channel is disposed on the plate's underside and has at least one second opening, such that the first opening of the first separation channel and the second opening of the second separation channel are interconnected, wherein the device has a cover that at least partially seals the topside or the underside, or a combination thereof, wherein the cover is a further plate which comprises a surface facing the plate on which the second separation channel is arranged, wherein the cover at least partially seals the underside, wherein the first opening of the first separation channel is sealed by a permeable partition wall, wherein a plurality of second separation channels are present, and wherein the second separation channels are capillary separation channels that extend in parallel; and using the device for analyzing samples, or isolating, cleaning and recovering chemical substances utilizing the device.

20. The method as claimed in claim 19, wherein the chemical substances are RNA, DNA or a protein or a combination thereof.

* * * * *